US005893834A

United States Patent [19]
Duchamp

[11] Patent Number: 5,893,834
[45] Date of Patent: Apr. 13, 1999

[54] SELF-FILLING BLOOD COLLECTION DEVICE

[75] Inventor: Jacky G. Duchamp, Spofford, N.H.

[73] Assignee: SIMS Portex Inc., Keene, N.H.

[21] Appl. No.: 08/637,489

[22] Filed: Apr. 25, 1996

[51] Int. Cl.⁶ ............................................. A61B 5/00
[52] U.S. Cl. ................................... 600/576; 600/573
[58] Field of Search ............................ 128/760, 765; 422/100; 604/195

[56] References Cited

U.S. PATENT DOCUMENTS

| | | |
|---|---|---|
| 4,228,808 | 10/1980 | Marsoner . |
| 4,595,021 | 6/1986 | Shimizu et al. ............ 600/573 |
| 4,703,763 | 11/1987 | McAlister .................. 600/578 |
| 4,877,585 | 10/1989 | Perlman ...................... 422/100 |
| 5,054,498 | 10/1991 | Melet .......................... 600/583 |
| 5,086,783 | 2/1992 | Macors et al. ............... 128/765 |
| 5,195,985 | 3/1993 | Hall ............................. 604/195 |
| 5,325,867 | 7/1994 | Skrabal et al. . |
| 5,373,855 | 12/1994 | Skrabal et al. . |
| 5,386,834 | 2/1995 | Schwarz . |
| 5,463,910 | 11/1995 | Burns et al. . |

*Primary Examiner*—Max Hindenburg
*Assistant Examiner*—Pamela L. Wingood
*Attorney, Agent, or Firm*—Louis Woo

[57] ABSTRACT

A self-filling blood collection device has a frusto-conical body through which a channel extends. The body is formed to have a lure end to mate with a needle and another end that is fitted with a hydrophilic filter that allows air to pass through but is self-sealing when exposed to fluid. The cavity volume of the channel is configured to accept different minute amounts of blood for testing. An insert may be fitted within the channel of the device to decrease the cavity volume so that a smaller amount of blood is collected. Once punctured with a needle attached to the lure end of the device, blood from the patient will self-fill the channel of the device due to the blood pressure of the patient. A vent cap may be added to the device to make it adaptable to be used with all types of blood analyzer equipment.

16 Claims, 3 Drawing Sheets

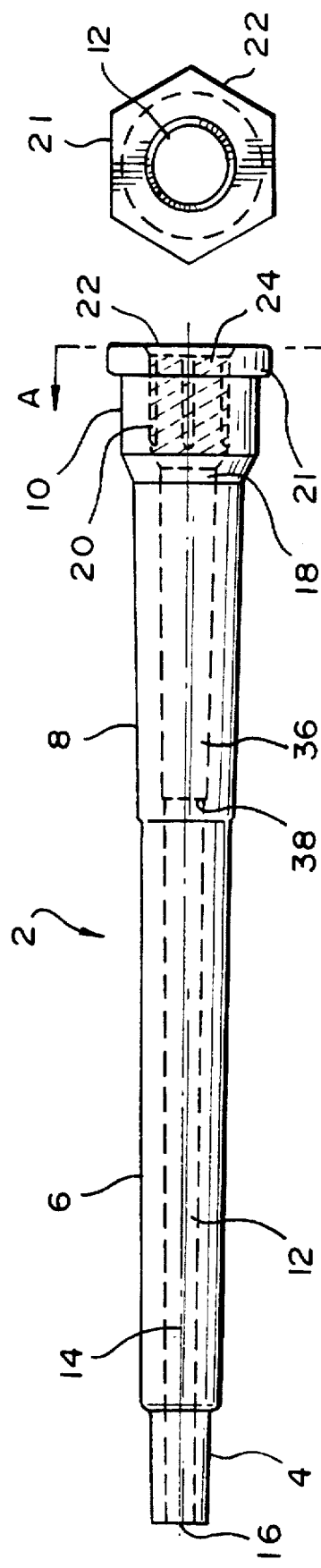
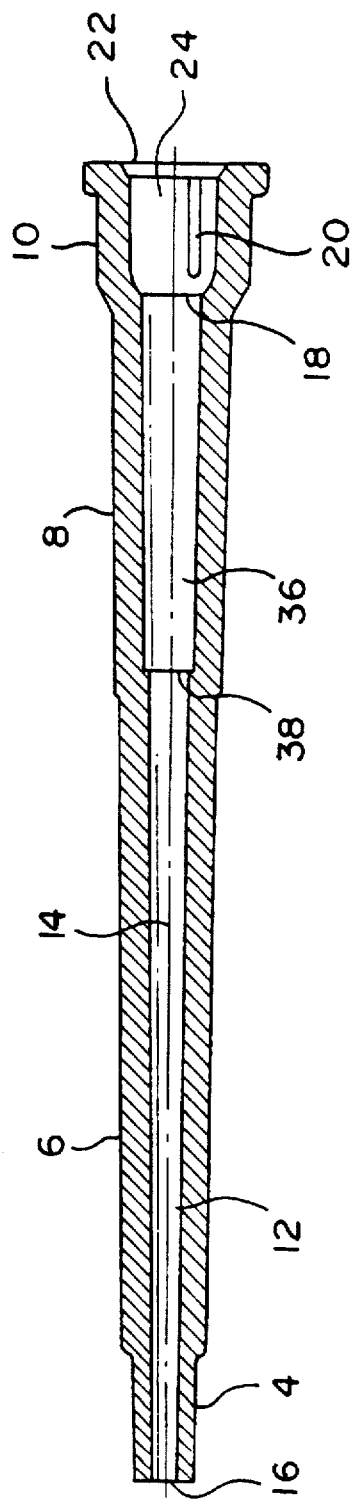

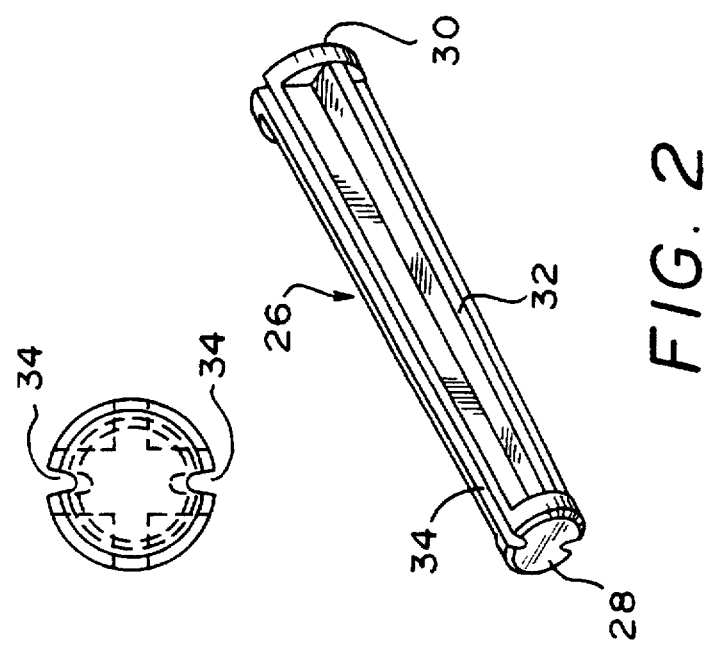
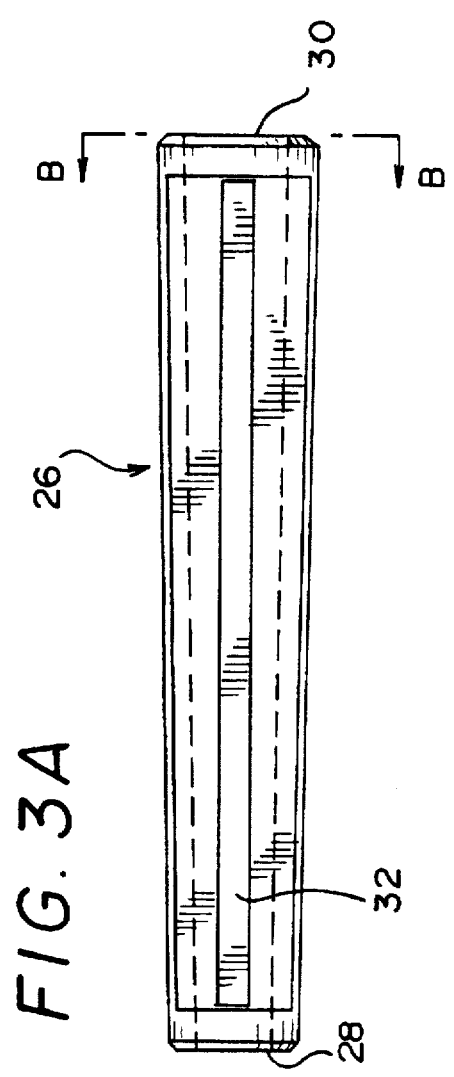
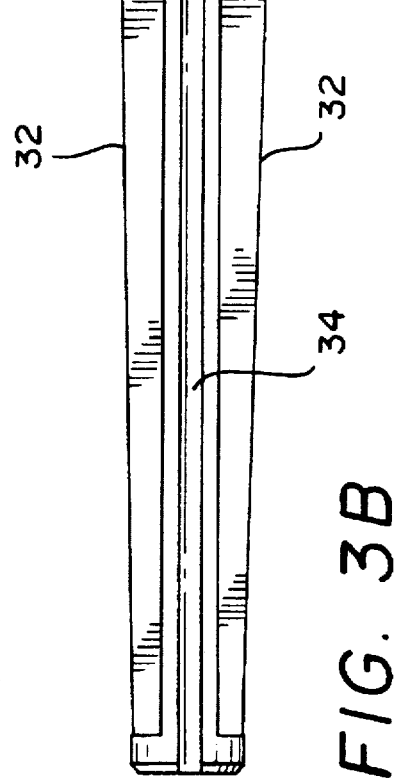

SELF-FILLING BLOOD COLLECTION DEVICE

FIELD OF THE INVENTION

The present invention relates to blood withdrawing devices and particularly to a blood-drawing device that is usable to withdraw a small amount of blood from patients who are hard to prick with conventional devices such as neonates especially.

BACKGROUND OF THE INVENTION

With the emergence of new blood gas analyzers that are capable of measuring a large number of different parameters from a small amount of whole blood, such as for example 200 μl., and the demand by the populace to cut or lower the cost of health care, in the field of arterial blood gas testing, the focus is on devices that are easy to use, yet technologically advanced. In other words, in the blood gas, electrolyte, metabolite, co-oximetry test field, the drive is toward blood collection devices that collect only a minute amount of blood and that are compatible with all the blood gas analyzers and/or co-oximeters.

Furthermore, for patients who are difficult to take blood from, for example such as neonates or older patients, there is a definite need for a reliable blood-drawing device that is designed to withdraw only a tiny amount of blood, such as for example 500 μl (0.5 cc) or less.

One such proposed product is disclosed in U.S. Pat. No. 5,386,834. In particular, this device comprises a protective tube into which are mounted two concentric glass capillaries. The protective tube is open at one end whereat a tapered member is mounted. This tapered member has an opening through which one end of a first of the capillaries extends. The other end of the first capillary is held by a connecting member located at the closed end of the protective tube. The second capillary also has one of its ends attached to the connecting member, which holds the respective ends of both capillaries in position and in communication with each other. The other end of the second capillary is held in place by the mounting member and is in open communication with the interior of the protective tube. There are two ventilation bores in the protective tube.

In operation, a cannula is connected to the exposed end of the first capillary. Once the patient is punctured by the cannula, blood is collected by means of capillary action and possibly blood pressure into the first capillary, and then the second. The phlebotomist has to make sure that a sufficient amount of blood is collected in the first capillary, so that there will be a sufficient amount of blood for evaluation. Since the second capillary has an open end, blood always overflows the open end of the second capillary into the protective tube, and in an extreme condition, possibly leaks out of the ventilation holes. A scenario of such happening is, for example, when the phlebotomist fails to notice that the collected blood has reached the end of the second capillary.

In addition to the real chance that possibly contaminated blood may leak out of the protective tubing, the flow of blood into the '834 device takes some time, since the respective diameters of the capillaries are rather small and each length of the capillaries is relatively long. So, too, since the amount of required blood to be collected may differ depending on the type of test being run, the '834 device needs to have different sized capillaries, for example one for 250 μl and one for 500 μl. And since the capillaries, as well as the protective tube are clear, a phlebotomist may mistake the larger-sized device from the smaller one once filled.

Further, since the capillaries are made of glass, they are easily breakable. Furthermore, the structure of the '834 device is such that it is adaptable only to certain types of blood gas analyzers.

There is therefore a need for an inexpensive, yet reliable blood-collecting device that is suitable for collecting an adequate yet minute amount of blood from patients who require that there be minimal trauma.

SUMMARY OF THE INVENTION

The present invention is a self-filling blood collection device (with a sufficient amount of arterial/venous blood pressure such as for example higher than 20 mmHg) that is suitable to withdraw a predetermined amount of blood from any patient with a blood pressure higher than 20 mmHg. The self-filling blood-drawing device of the instant invention has a one-piece frusto-conical body that has a longitudinal channel extending therethrough. One end of the body is formed as a lure for mating with a conventional type of needle or cannula. The other end of the body, which may be referred to as a base end, is fitted with an hydrophilic filter such as a FILTER-PRO™ filter by the Smith's Industries Medical Systems (SIMS) Company for example. This hydrophilic filter allows gases such as air to pass through but yet prevents fluids such as blood from passing therethrough because the hydrophilic filter material used has the characteristic that its fibers would expand to form a seal when exposed to fluid. Accordingly, once the filter material is exposed to blood, it reacts therewith to become an airtight barrier seal to the blood. Thus, it prevents outside air from contaminating the blood sample collected in the channel.

The channel of the body is designed to have a predetermined cavity volume so that, once the appropriate needle is connected to the lure end and inserted into the patient, the blood pressure (arterial or venous) of the patient will force blood into the channel. As blood fills the channel, air is expelled through the hydrophilic filter so that the channel is anaerobically filled with the appropriate amount of blood.

To provide a different predetermined cavity volume in the channel, a non-absorbent insert having at least one groove (or flash channel) extending longitudinally therealong is fitted into the portion of the channel proximate to the filter. Thus, an insert fitted device may have a capacity volume of 250 μl, for example, whereas a non-insert filled device may have a cavity volume of 500 μl, for example. Since there is at least one longitudinal flash channel through or along the length of the insert, at least one path is provided for both the blood and the air to travel from the front of the channel to the filter, so that blood drawn with the insert-fitted device likewise fills the insert-fitted channel anaerobically.

To enable a user to easily determine the cavity volume of the device, a colorant is added to the insert so that a user can readily see it in the device. This is because the body of the device is molded from a clear material that does not interfere with the chemico-physical properties of the blood samples.

To ensure that the collected blood does not clot within the channel, some type of anticoagulant that enables accurate readings of PH/blood gases, electrolytes, metabolites, co-oximetry etc. is provided in the channel.

Given that the blood collection device of the instant invention has a conventional type of lure, it is adaptable to be used with all types of blood gas analyzers and co-oximeters.

The blood collection device of the instant invention therefore provides an improved device that is simple to make and capable of obtaining different predetermined volumes of blood adaptable to be used with all types of blood gas analyzers and co-oximeters.

BRIEF DESCRIPTION OF THE DRAWINGS

The above-mentioned objectives and advantages of the instant invention will become more apparent and the invention will be best understood with reference to the accompanying drawings, in which:

FIG. 1A is a side view of the blood collecting device of the instant invention;

FIG. 1B is a cutaway cross-sectional view of the FIG. 1A device;

FIG. 1C is a view along direction A—A of the FIG. 1A device;

FIG. 2 is a perspective view of an insert of the instant invention device;

FIG. 3A is a side view of the FIG. 2 insert;

FIG. 3B is another view of the FIG. 2 insert with the groove extending therealong being shown;

FIG. 3C is an end view of the FIG. 2 insert along line B—B thereof;

DETAILED DESCRIPTION OF THE INVENTION

Figure 4A:
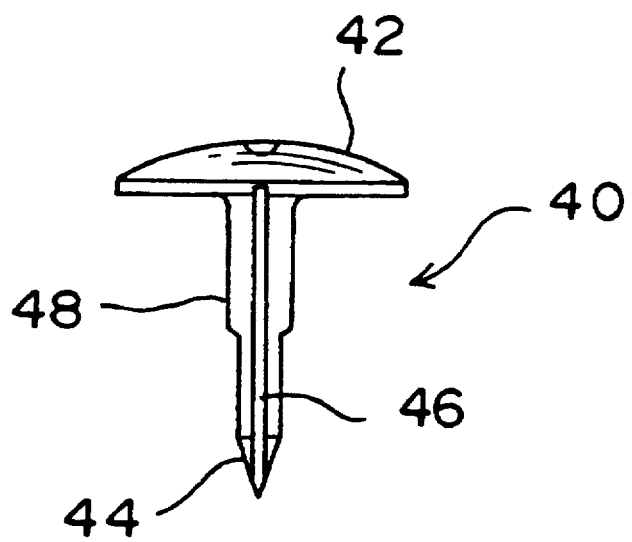
FIG. 4A is a side view of a vent cap, or puncher, being bundled with the blood collection device of the instant invention which makes the blood collection device adaptable to be used with all types of blood testing equipment, including those that are not equipped with needle or probe samplers.

With reference to FIGS. 1A–1C, the present self-filling blood collection device invention is shown to have a one piece body having a substantially frusto-conical shape. Body 2 may be formed by injection molding from a clear, gas impermeable, substantially rigid and nonflexible plastic material such as, for example, K-Resin from the Phillips Petroleum Company. Body 2 is shown to be divided into a number of sections, among which is a lure end 4. A main body section 6 extends from the end of lure end 4 to another section that, for this discussion, is designated 8. Body 2 further has an end base section 10 which is shown to have a diameter that is slightly bigger than the other sections.

Extending about longitudinal axis 14 through all sections of body 2 is a channel 12. Channel 12 is formed to have a given cavity volume such as, for example, approximately 0.5 cc. or 500 µl from end 16 of lure section 4 to dotted line 18 at base section 10, and approximately 0.25 or 250 µl from end 16 to line 38. Note, however, that device body 2 may be configured such that other predefined cavity volumes for channel 12 may also be effected. In other words, channel 12 is configured to handle a cavity volume that is adaptable for storing different volumes of blood. For the instant blood collection device, lure end 4 is formed to have a conventional dimension such that most, if not all, types of needles or cannulas can be matingly fitted thereto.

Base section 10, as was mentioned previously, has a somewhat larger diameter than channel 12. Formed at base section 10 are a number of ribs 20 and a hexagonal flange 21, which prevents body 2 from rolling when it is placed onto a surface. Base end section 10 has a surface 22 that is open to the environment, and in fact, is a continuation of channel 12. A self-sealing hydrophilic polyethylene type filter such as the FILTER-PRO™ filter of the SIMS Company for example, designated 24, is fitted into the cavity at base end section 10. Filter 24 has the characteristic that its pores would substantially close when a fluid impregnates it. Accordingly, filter 24 allows gases such as air to pass therethrough while channel 12 is being filled by a fluid, and yet will prevent the fluid such as blood from passing by self-sealing when the fluid comes into contact with it. This characteristic of filter 24 therefore enables the collected sample to be preserved anaerobically.

In operation, to use the instant invention blood collection device, a needle is fitted to lure end 4. The needle is then inserted into the patient, possibly in one of the patient's arteries or veins. The blood pressure (arterial or venous) of the patient will then provide the driving force that enables the blood of the patient to flow into channel 20 of device 2. As blood fills channel 12, air that was in channel 12 is forced out of channel 12 through filter 24. Thus, without the phlebotomist having to do anything else, the blood of the patient will self-fill device 2, therefore eliminating the risk of air contamination. Since filter 24 is made of hydrophilic material, such as self-sealing polyethylic for example which closes in contact with blood, blood is prevented from passing therethrough as filter 24 in essence becomes a plug. Once channel 12 is filled with blood, no more blood is withdrawn from the patient.

The fact that the hydrophilic filter 24 allows air to pass through and yet prevents blood from passing means that channel 12 is filled with the patient's blood anaerobically. And since the volume cavity of channel 12 is predefined, a predetermined volume of blood is collected within device 2. Although 500 µl is a standard required volume that is deemed to be sufficient for a number of tests by blood gas analyzers and co-oximeters, the volume capacity of channel 12 may be easily reconfigured for different volumes, if necessary, insofar as device 2 is a one piece injection molded device.

Once channel 12 of device 2 is filled with blood, the needle is withdrawn from the patient and disposed of. A cap may then be placed at lure end 4 so that device 2 may be transported in a watered ice bed to any one of a number of blood gas analyzers and co-oximeters. Lure end 4 may then be presented to the input port of any one of those blood gas analyzers so that the blood within channel 12 can be tested.

A vent cap or puncher is preassembled in the filter to enable the blood collection device of the instant invention to be usable with all types of blood gas analyzers and co-oximeters, even those that do not have a needle or probe sampler. For equipment that do not feature a needle or probe-like sampler, the practitioner can pierce hydrophilic filter 24 with the vent cap by simply applying a pressure on the cap head to create a vent through the filter. The equipment can then aspirate the blood sample, which has been preserved anaerobically, by means of a vacuum mode for example.

Figures 4B, 4C:
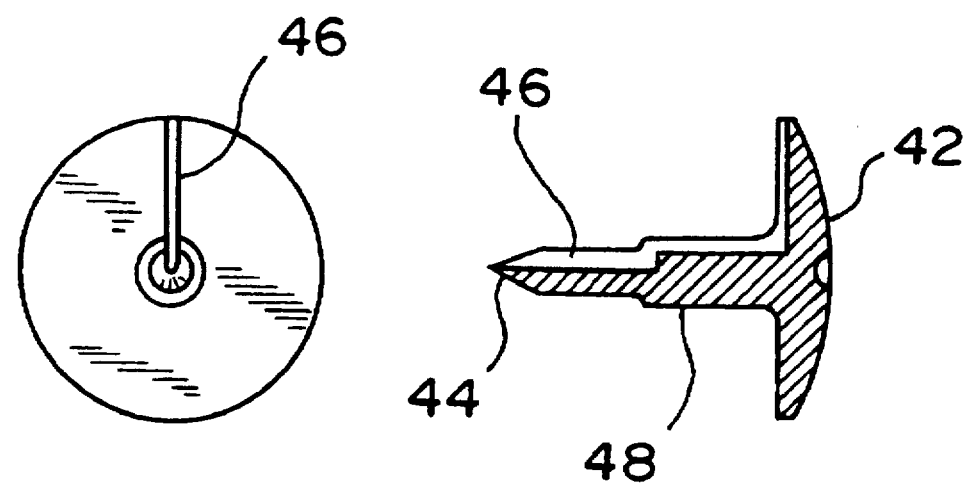
FIG. 4B is a semi cut-away cross sectional view of the FIG. 4A vent cap showing the path through which a vent may be formed when the vent cap, upon application of a force, pierces the filter material fitted to the blood collection device of the instant invention.
FIG. 4C is an end view of the vent cap of FIGS. 4A and 4B.

Such a vent cap is illustrated in FIGS. 4A–4C. As shown, vent cap 40 is shaped to a have a top 42 and a sharp end 44 extending therefrom. A groove 46 extends from tip 44 to top 42 of puncher 40. Vent cap 42 is dimensioned such that the body thereof, designated 48, is smaller than the diameter of filter 24. Vent cap 40 can be preassembled in filter 24, for example by having its tip 44 and a portion of its body 48 inserted thereinto. Thus, once blood has been collected within channel 12 and filter 24 has self-sealed into a plug for sealing the blood therein, if the blood collection device of the instant invention were to be used with an equipment that does not have a "needle of proble-like", sampler, the sealed filter 24 can be punctured by applying a force to the head 42 of vent cap 40 so that a vent is created through filter 24 by means of groove 46 extending from tip 44 to top 42 of vent cap 40. To enhance the distinctiveness of vent cap 40, vent cap 40 may be made from a colored plastic, such as for example a supressed red S.A.N. plastic.

Note that even though a conventional type needle may be used with device 2, a type of needle assembly such as the NEEDLE-PRO™ device that has a sheath adaptable to envelop and retain the contaminated needle can also be used. Such NEEDLE-PRO™ device is made by the SIMS Company.

Device 2 self-fills at a fast rate, much faster relative to the above-noted prior art capillary device. This is due to its configuration, such as for example its frusto-conical shape, and the relatively large diameter of channel 12. Given a noncompressible fluid such as blood at a given pressure, such as for example between 200 mmHg to 20 mmHg, for device 2 having an internal diameter of 0.1026 inches, 250 μl of blood can be collected at a much faster rate than the prior art capillary-type blood collector. To prevent the collected blood from clotting, channel 12 may contain some type of anticoagulant, such as heparin, that will enable accurate measurements of PH/Blood Gases electrolytes, metabolites, co-oximetry, etc.

As was mentioned previously, the cavity volume of channel 12 can be reconfigured. In practice, since different types of tests require different volumes of collected blood, a volume that is less than the conventional cavity volume of device 2 having channel 12 running longitudinally therealong is needed. Such a reduced cavity volume may be, for example, 250 μl.

To achieve a reduced cavity volume, device 2 may be fitted with an insert such as 26 shown in FIG. 2. As more clearly illustrated in FIGS. 3A–3C, insert 26 comprises a substantially solid conically shaped insert that may be made from any non-porous plastics such as for example polypropylene. Insert 26 has two end surfaces 28 and 30. To provide rigidity, there are at least two ribs 32 extending longitudinally between end surfaces 28 and 30. There is also at least one and possibly more grooves (or flash channels) 34 extending longitudinally along the length of insert 26.

In combination with body 2 of the blood collection device, insert 26 is fitted substantially in section 8 of body 2, particularly in the space of channel 2 designated 36. The dimension of insert 26 is predefined so that once it is fitted within channel 12 of the device, a predetermined cavity volume for device 2 is provided. Such predetermined cavity volume obviously would be less than the cavity volume of a non-insert fitted device.

Given groove(s) 34 of insert 26, the operation of device 2 remains the same. That is, blood from the patient will self-fill the cavity volume of channel 12 by pushing the air in channel 20 towards filter 24 via groove(s) 34. Like before, once blood has filled channel 12 including the space defined by groove 34, the blood collection is stopped. The insert-filled blood collection device is then withdrawn from the patient, the contaminated needle removed, lure end 4 capped, and the device put into a watered ice bed to be transported to a blood gas analyzer and/or co-oximeter for testing.

Since it is beneficial for the user, i.e., the phlebotomist, to determine how much blood has filled channel 12 of device 2 at any given time, the body of device 2 should be clear. This is achieved by injection molding the body using a clear chemically neutral or inert plastic such as for example the above-mentioned K-Resin.

To provide the user an easy indication that device 2 has a given cavity volume, insert 26 has a colorant, such as for example blue, added thereto so that a device that is insert-fitted can readily be ascertained by the user to have a smaller cavity volume than a device that is non-insert fitted.

Note that even though insert 26 is shown to be fitted within channel 12 of device 2 at position 36 thereof, it should be appreciated that something other than insert 26 may also be fitted thereto. For example, instead of using insert 26, filter 24 may be configured to have a shape that is a combination of space 36 and the space shown to fill base end section 10 in FIGS. 1A and 1B. Alternatively, hydrophilic filter 24 may be configured or selected to only fit within space 36. Yet another alternative choice may be that instead of a single piece filter 24 that extends from line 38 to base 22, a first filter may be fitted somewhere proximate to line 38, with a void being left in space 36, before a second filter such as 24 is fitted at base section 10. Both filters would be made of self-sealing polyethylene, such as those manufactured by POREX technologies for example.

Inasmuch as the present invention is subject to many variations, modifications and changes in detail, it is intended that all matter described throughout the specification and shown in the accompanying drawings be interpretated as illustrative only and not in a limiting sense. Accordingly, it is intended that the invention be limited only by the spirit and scope of the hereto appended claims.

I claim:

1. A self-filling blood drawing device comprising:
    a one piece frusto-conically shaped body having a longitudinal channel extending therethrough and a first lure end for accepting a needle for pricking a patient, said channel being configured to have a predetermined cavity volume adaptable for storing different amounts of blood from the patient; and
    a hydrophilic, self-sealing polyethylene filter selected to have a shape for defining said predetermined cavity volume of said channel fitted to other end of said body, said filter permitting air but stopping blood from passing therethrough;
    wherein once the patient is pricked by said needle, blood from the patient is forced into said predetermined cavity volume of said channel to fill said channel anaerobically by the blood pressure of the patient.

2. The device of claim 1, further comprising:
    an insert fitted to the portion of said channel proximate to said hydrophilic filter, said insert having at least one groove longitudinally extending therealong so that blood withdrawn from the patient flows to said hydrophilic filter and air in said channel passes through said filter via said groove, said insert effecting the cavity volume of said channel to store a lesser amount of blood within said channel.

3. The device of claim 1, wherein said body is made from a clear material by injection molding.

4. The device of claim 1, further comprising a small amount of heparin added to said channel to prevent clotting of the blood stored therein.

5. The device of claim 2, wherein said insert has a colorant added thereto so that a device fitted with said insert provides an indication that it is an insert fitted device.

6. The device of claim 1, wherein said channel has a cavity volume of substantially 500 μl.

7. The device of claim 2, wherein said channel has a cavity volume of substantially 250 μl.

8. The device of claim 1, further comprising:

a puncher fitted relative to but not through said filter, said puncher being used to puncture said filter after said filter has self-sealed upon exposure to blood to effect a vent through said filter so that said device is adaptable to be used with blood analyzing equipment that were not designed to be used with probe-like blood collection devices.

9. Apparatus for withdrawing blood from a patient, comprising:

a one piece frusto-conical shaped body having a lure end, a base end and a channel extending longitudinally through said body to connect said ends, said lure end accepting a needle for invasively contacting a patient to withdraw blood from the patient to fill said channel, said channel being configured to have a cavity volume adaptable for storing a greater and a smaller amount of blood from the patient; and a hydrophilic, self-sealing filter selected to have a shape for defining said cavity volume of said channel fitted at said base end of said body, said filter permitting air to pass but preventing blood from passing therethrough so that a given amount of blood of the patient corresponding to the configured cavity volume of said channel is automatically forced into and anaerobically stored in said channel due to the blood pressure of the patient.

10. Apparatus of claim 9, further comprising:

an insert fitted within said channel adjacent to said hydrophilic filter at said base end of said body, said insert being substantially solid and having at least one groove longitudinally extending along its outer circumferential surface so that blood withdrawn from the patient and air in said channel can pass to said filter via said groove, said insert effecting the cavity volume of said channel to store the smaller amount of blood in said channel.

11. Apparatus of claim 9, wherein said body is made from a clear material by injection molding.

12. Apparatus of claim 9, further comprising heparin deposited into said channel to prevent clotting of the blood stored in said channel.

13. Apparatus of claim 10, wherein said insert has a colorant added thereto so that a device fitted with said insert provides a definitive indication that it is to be used for withdrawing a smaller amount of blood from a patient than a non-insert fitted device.

14. Apparatus of claim 9, wherein said channel has a cavity volume of substantially 250 μl.

15. Apparatus of claim 10, wherein said channel has a cavity volume of substantially 500 μl.

16. The device of claim 9, further comprising:

a puncher fitted relative to but not through said filter, said puncher being used to puncture said filter after said filter has self-sealed upon exposure to blood to effect a vent through said filter so that said device is adaptable to be used with blood analyzing equipment that were not designed to be used with probe-like blood collection devices.

* * * * *